United States Patent [19]

Stuart et al.

[11] Patent Number: 5,695,965
[45] Date of Patent: Dec. 9, 1997

[54] NEUROSPORA EXPRESSION SYSTEM

[75] Inventors: W. Dorsey Stuart, Kaneohe; John M. Ivy, Kailua, both of Hi.; Kenneth Koo, Encino, Calif.

[73] Assignee: Hawaii Biotechnology Group, Inc., Aiea, Hi.

[21] Appl. No.: 896,455

[22] Filed: Jun. 2, 1992

Related U.S. Application Data

[63] Continuation of Ser. No. 492,666, Mar. 13, 1990, abandoned.

[51] Int. Cl.⁶ .................................................. C12P 21/02
[52] U.S. Cl. ..................... 435/69.1; 435/69.6; 435/69.4; 435/69.52; 435/172.3; 435/254.4; 435/320.1; 435/219; 536/24.1
[58] Field of Search ............................... 435/69.1, 172.3, 435/252.7, 69.4, 69.52, 69.6, 254.4, 320.1, 219; 536/24.1

[56] References Cited

U.S. PATENT DOCUMENTS

| | | | |
|---|---|---|---|
| 4,399,216 | 8/1983 | Axel et al. | 435/6 |
| 4,486,533 | 12/1984 | Lambowitz | 435/172.3 |
| 4,666,847 | 5/1987 | Alford et al. | 435/252.33 |
| 4,757,020 | 7/1988 | Beppu et al. | 435/253 |
| 5,187,079 | 2/1993 | Free et al. | 435/69.1 |

FOREIGN PATENT DOCUMENTS

| | | |
|---|---|---|
| 0 099 226 | 1/1984 | European Pat. Off. . |
| 0 177 243 | 4/1986 | European Pat. Off. . |
| 0 215 539 | 3/1987 | European Pat. Off. . |
| 215594 | 3/1987 | European Pat. Off. . |
| 225078 | 6/1987 | European Pat. Off. . |
| 238023 | 9/1987 | European Pat. Off. . |
| 249350 | 12/1987 | European Pat. Off. . |
| 2200118 | 7/1988 | United Kingdom . |
| 86/06097 | 8/1986 | WIPO . |
| 87/02670 | 5/1987 | WIPO . |
| 89/01969 | 3/1989 | WIPO . |

OTHER PUBLICATIONS

Weiss et al. (1985) Conference Paper Dept of Chem & Biochem @UCLA (279–92).

Cullen et al. (1986) Trends Biotechnol. vol. 4(11) pp. 285–288.

Collins et al. (1990) Eur. Congr. Biotechnol. (5 Meet., 207–10).

Abstract of PCT 86/025462 (Shiseido KK).

Britz (1987) Austral. J. Biotechnol 1(3), 29–40.

T. Smith, (1989) Proceed. Natl. Acad. Sci, USA 86, 7063–7066.

David J. Smith, et al., "Cloning and Heterologous Expression of the Penicillin Biosynthetic Gene Cluster From Penicillium Chrysogenum," *Bio/Technology*, vol. 3, Jan. 1990, 39:41.

Nigel S. Dunn–Coleman, et al., "Commercial Levels of Chymosin Production By Aspergillus," *Bio/Technology*, vol. 9, Oct. 1991, pp. 976–981.

A. Upshall, et al., "Secretion of Active Human Tissue Plasminogen Activator From the Filamentous Fungus Aspergillus Nidulans," *Bio/Technology*, vol. 5, Dec. 1987, pp. 1301–1304.

A. Upshall, et al., "Molecular Manipulation of and Heterologous Protein Secretio From Filamentous Fungi," *Molecular Industrial Mycology*, (Marcel Dekker, Inc. 199 Leong and Berka (eds), Chapter 2, pp. 31–43.

R. Wayne Davies, "Molecular Biology of a High–Level Recombinant Protein Production System in Aspergillus," *Molecular Industrial Mycology*, (Marcel Dekker Inc. 1991), Leong and Berka (eds), Chapter 3, pp. 45–81.

"Japan Roundup," *Bio/Technology*, vol. 8, Mar. 1990, p. 188, Column 3.

D. James Ballance, "Transformation Systems for Filamentous Fungi and an Overview of Fungal Gene Structure", *Molecular Industrial Mycology*, (Marcel Dekker, Inc. 1991), Leong & Berka, (eds) Chapter 1, pp. 1–29.

A. Clements, et al., "Strain–Dependent Difference in Transformation Frequency," *Fungal Genetics Newsletter*, No. 32:6–7 (1985).

Staben, et al., "Use of a Bacterial Hygromycin B resistance Gene as a Dominant Selectable Marker in Neurospora crassa Transformation," *Fungal Genetics Newsletter* No. 36, Jun. 1989.

Gwynne et al., 1987, *Bio/Technology*, vol. 5: 713–719.

Vollmer et al, 1986, *PNAS*, vol. 83: 4869–4873.

*Biological Abstracts*, vol. 87, Abstract No. 125966, 1989, McNally et al. 1988, Curr. Genet., 14(6): 545–552.

McCaman et al. "Enzymatic Properties and Processing of Bovine Prochmyosin Synthesized in *Escherichia coli*.", J. Biotech. 2:177–190 (1985).

(List continued on next page.)

*Primary Examiner*—James Ketter
*Attorney, Agent, or Firm*—Rae-Venter Law Group, P.C.

[57] ABSTRACT

*Neurospora crassa* transformations are employed for production of heterologous proteins, where DNA constructs are prepared using a foreign gene under transcriptional and translational regulatory regions functional in Neurospora. A functional signal sequence is provided for secretion of the heterologous gene product. An auxotrophic Neurospora host is employed and transformed by the combination of the subject construct and a complementing gene. The resulting transformants provide for efficient secretion of the heterologous product.

31 Claims, No Drawings

OTHER PUBLICATIONS

Kawaguchi et al. "Production of Chymosin in *Escherichia coli* Cells and Its Enzymatic Properties", *Agric. Biol. Chem.* 51:1871–1877 (1987).

Cullen et al. "Controlled Experssion and Secretion of Bovine Chymosin in *Aspergillus nidulans*", Bio/Technology 5:369–376 (1987).

Anon., "Genencor Films on rDNA Cheese Enzyme". *Biotechnology News*, 9:1–2.

Smith et al. "Heterologous Protein Secretion from Yeast", *Science* 229:1219–1223 (1985).

Harkki et al. "A Novel Fungal Expression System: Secretion of Active Calf Chymosin from the Filamentous Fungus *Trichoderma reesei*", Bio/Technology, 7:596–603 (1989).

Klessen et al., "Complete Secretion of Activable Bovine Prochymosin by Genetically Engineered L forms of *Proteus mirabilis*", Appl. Environ. Microbiol. 55:1009–1015, (1989).

Berg et al., "*Kluyveromyces* as a Host for Heterologous Gene Expression: Expression and Secretion of Prochymosin", Bio/Technology 8:135–139 (1990).

Christensen et al, "High Level Expression of Recombinant Genes in *Aspergillus oryzae*", *Bio/Technology,* 6:1419–1422, (1988).

Upshall, et al., "Secretion of Active Human Tissue Plasminogen Activator from the Filamentous Fungus *Aspergillus nidulans*", Bio/Technology 5:1301–1304, (1987).

Orbach et al., "Cloning and Characterization of the Gene for β-Tubulin from a Benomyl–Resistant Mutant of *Neurospora crassa* and Its Use as a Dominant *Selectable Marker*", Mol. Cell. Biol. 6: 2452–2461, (1986).

McNally, M. T. and S. J. Free, "Isolation and Characterization of a *Neurospora* Glucose–Repressible Gene", Current Genetics, 14:545–551, (1988).

K. Hayenga, et al., Expression and Secretion of Bovine Calf Chymosin by *Aspergillus nidulans, Journal of Cell Biology Supplement,* p. 274 (1986).

NEUROSPORA EXPRESSION SYSTEM

CROSS-REFERENCE TO RELATED APPLICATIONS

This application is a continuation of U.S. application Ser. No. 07/492,666, filed Mar. 13, 1990, now abandoned.

TECHNICAL FIELD

The field of this invention is DNA constructs for use in Neurospora for protein expression.

BACKGROUND

Molecular biology has offered the opportunity to produce a wide variety of proteins from disparate sources. As various expression constructs have been developed, as well as expression systems with different hosts, numerous problems have been encountered affecting the level of expression, stability of the DNA construct, nature of the product, and yield of product. In addition to the above mentioned concerns, there has been an interest in secretion, where the product of interest may be joined to a signal peptide for secretion, and in post-translational processing, where the product may be further processed by glycosylation, acylation, phosphorylation, peptide cleavage, or the like. Further considerations include the nature of the folding of the protein product, which in many cases may be correlated with biological or physiological activity.

There is substantial interest in developing expression systems for heterologous proteins, which employ a host which: (1) may be readily fermented with an inexpensive medium which is used efficiently, (2) produces the product in high yield, (3) is capable of efficient secretion, and (4) allows for ease of isolation and purification of a product having a high level of biological activity.

Relevant Literature

Descriptions of filamentous fungal transformation systems include U.S. Pat. No. 4,486,533, EPA 0 215 539, EPA 0 215, 594, EPA 0 177 243, JP60248181, EPA 0 172 506, EPA 0 220 689, WO86 06097, EPA 0 225 078, EPA 0 249 350, GB2,200,118, and EPA 0 278 335.

Gwynne et al. (1987) Bio/Tech. 5, 713–719 report the use of Aspergillus nidulans to produce human interferon and bacterial endoglucanse, Upshall et al., (1987) ibid 5, 1301–1304 employ the same fungus to produce active human tissue plasminogen activator. Cullen et al., (1987) ibid 5, 369–376 employ the same fungus to produce active bovine chymosin. Harkki et al., (1989) ibid 9, 596–603 employ the fungus Trichoderma reesei to produce active bovine chymosin.

SUMMARY OF THE INVENTION

Neurospora expression systems are provided, where DNA comprising a chimeric construct of a heterologous open reading frame under the transcriptional regulation transcriptional initiation and termination regulatory regions functional in a Neurospora host cell is employed. Co-transformation of the construct with a marker gene, particularly one providing complementation of an auxotrophic mutant, provides for transformants which efficiently produce the heterologous protein.

DESCRIPTION OF SPECIFIC EMBODIMENTS

Methods and compositions are provided for production of heterologous proteins in a Neurospora host. DNA constructs are prepared which employ a heterologous open reading frame and endogenous transcriptional regulatory regions. The regulatory regions are selected for high levels of expression of a heterologous gene and for transcriptional termination and polyadenylation, while the heterologous open reading frame encodes a signal which provides efficient secretion and processing of the heterologous protein.

Transformation of the Neurospora host may be achieved with spheroplasts, where a co-transforming DNA provides a marker allowing for selection of transformed host cells after allowing for regeneration of the cell wall. The transformed host may then be cultured and used for production and secretion of the heterologous product.

The host is Neurospora, particularly N. crassa. A number of transcriptional promoters may be used in accordance with the subject invention. These transcriptional promoters from Neurospora include the β-tubulin gene, the grg-1 gene, invertase, etc. These genes comprise a transcriptional promoter, translational initiating and terminating codons, a translated sequence, transcriptional stop signal, and a polyadenylation signal. Protein encoded by the translated sequence may or may not include a secretion signal peptide. Secretion signal sequences which may be used include signal sequences from the genes that encode proteins secreted from Neurospora e.g., invertase, glucoamylase, nucleases, cellulases, acid phosphatase, alkaline phosphatase, etc., and from heterologous proteins whose secretion signals function in Neurospora, e.g., bovine chymosin. Such a heterologous secretion signal may be derived from the heterologous protein intended for production or from a second heterologous protein other than the one desired for production. The heterologous gene may be from any source, particularly a mammalian source. Among mammalian genes of interest are blood proteins, such as Factor VIII, tissue plasminogen activator, complement factors, serum albumin, etc.; growth factors, growth hormones, interleukins, etc.: surface membrane proteins, enzymes, structural proteins, synthetic proteins, or the like.

The subject constructs may be readily prepared in accordance with conventional methods. The various DNA fragments may be obtained from natural sources, may be synthesized, or combinations thereof. By appropriate manipulations, using restriction endonucleases, in vitro mutagenesis, the polymerase chain reaction, or the like, fragments may be manipulated to provide the appropriate sequences. Fragments having sticky or blunt ends or tailed with complementary sequences may be joined by ligation.

The DNA construct will contain in order: a transcriptional initiation regulatory region, a 5' transcribed but untranslated region, a translation initiating codon, a secretion signal-encoding sequence, a sequence encoding the protein product, a translational stop codon(s), and a transcriptional terminating region. The transcriptional initiation regulatory region will comprise the sequences associated with the promoter and an enhancer as appropriate. The 5' untranslated region may be derived from sequences normally contiguous to the Neurospora promoter, or from sequences 5' to the heterologous open reading frame, or may comprise a combination of the two. Next will be a sequence encoding a secretion signal, joined in translational reading frame to the heterologous open reading frame or gene. The open reading frame, with its termination codon(s) will be followed by the 3' untranslated region, normally a polyadenylation signal sequence, and a termination regulatory sequence that are functional in Neurospora. Where no signal sequence is present, the open reading frame will have its own initiation codon. Other DNA may or may not be present, depending upon convenience, effect of the other DNA on the efficiency of transformation and expression, and the like.

The transcriptional regulatory regions may be constitutive or inducible, particularly where physical or chemical agents are employed. Thus, temperature sensitive transcriptional initiation regulatory sequences may be employed, where the regulatory protein is responsive to changes in temperature. Alternatively, a chemical, such as a carbohydrate (e.g., glucose, sucrose, galactose) may affect the regulation.

Normally, the DNA construct is made in a vector which allows for the analysis of the construct or portions thereof at the various stages of preparation of the construct. Conveniently, the cloning is performed in *E. coli*, using conventional cloning vectors which comprise a replication system, a marker for selection of transformants, particularly resistance to a biocide, e.g., antibiotic, and may comprise one or more polylinkers for convenient insertion and removal of DNA sequences.

The subject construct is transformed into a Neurospora spheroplast employing cotransformation. Conveniently, the Neurospora may be a mutant which is unable to synthesize an essential metabolite, e.g., an amino acid, and the co-transforming DNA complements the auxotroph to prototropy. Various auxotrophic Neurospora mutants are available, such as his-2 (Fungal Genetics Stock Center No. 21).

Transformation can be achieved using spheroplasts in the presence of polyethyleneglycol in an isotonic medium comprising appropriate carbohydrates. The amount of DNA employed will generally range from about 1 to 5 µg per $10^7$ cells. After transformation, the cells are grown in medium that selects prototrophs, which may be further screened for the presence of the desired open reading frame, as well as expression of the heterologous protein.

The following examples are offered byway of illustration and not byway of limitation.

EXPERIMENTAL

MATERIALS AND METHODS

Strains

For recombinant DNA work, *E. coli* strains DH5α (Bethesda Research Laboratories [BRL]) and NM522 were used. *N. crassa* strain his-2; mtr (Stuart et al., 1988 Gene 30:198–203) was used for all work.

Culture Conditions

Standard culture conditions for *E. coli* (Maniatis et al., 1982 Molecular cloning, A laboratory manual, Cold Spring Harbor Laboratory, Cold Spring Harbor, N.Y.) and *N. crassa* (Davis and DeSerres, 1970 *Methods in Enzymology* 23:80–143) were used, with the exception that *N. crassa* transformants were cultured in broth containing 2% tryptone to suppress expression of extracellular proteases (Drucker, 1972, *J. Bacteriology* 110:1041–1049), and either a carbohydrate carbon source for *N. crassa* culture was eliminated or, for the grg-1 promoter constructs, fructose was substituted for sucrose.

Recombinant DNA

All manipulations of DNA were standard and can be found in Maniatis et al., 1982, supra and Ausubel et al., 1987, Current Protocols in Molecular Biology, John Wiley & Sons. Restriction and DNA modification enzymes were obtained from commercial sources: BRL, New England Biolabs, Pharmacia, Boehringer Mannheim, US Biochemicals, and Promega. DNA sequence analysis was by the dideoxynucleotide method (Sanger et al., 1977, *Proc. Natl. Acad. Sci. USA*, 74:5463–5467) using Sequenase™ (US Biochemicals) and the protocols recommended by the manufacturer.

Transformation of *N. crassa*

Transformation of *N. crassa* was by the method of Vollmer and Yanofsky, 1986 *Proc. Natl. Acad. Sci. USA*, 83:4869–4873). Briefly, conidia were harvested from 5–7 day cultures and converted to spheroplast by Novozyme (Novolabs) digestion in the presence of 1M sorbitol. Spheroplasts were mixed with 1–5 µg DNA in the presence of 50 µM spermidine, 5 mg/ml heparin, 40% PEG "4000", 1M sorbitol, and plated in Vogel's top agar containing 2.8% agar, 1M sorbitol, 2% sorbose, 0.02% inositol, 0.05% fructose, and 0.02% glucose. Transformants of the his-2; mtr strain were obtained with cosmid 6:11E containing a wild-type his-2 allele (Stuart et al., 1988 Gene 30:198–203) isolated from the Volmer cosmid gene library (Vollmer and Yanofsky, 1986, supra) and were detected by selecting for prototrophs on minimal Vogel's medium.

Milk Coagulation Assays

Milk coagulating activity of chymosin was determined according to the methods of Foltmann (*Methods in Enzymology* 19:421–436 (1970)) with minor modifications. We combined 0.2 ml of sample with 0.2 ml of 10% (w/v) Carnation skim milk in 50 mMCaCl$_2$ in a 1.5 ml microcentrifuge tube, which was incubated at 30° C. The time required to first see coagulation was recorded. Milk coagulating activity was tested in untreated and in acid treated culture media. Treatment at pH 2 rapidly converts prochymosin to pseudochymosin, and pH 4.5 treatment converts prochymosin to chymosin (Foltmann, 1970 supra). Both pseudochymosin and chymosin exhibit milk coagulating activity. pH adjustments were monitored using a pH meter. Samples were acidified and neutralized by adding HCl to samples containing 0.1M NaCl, incubating at room temperature 10 min, adding a volume of 5N NaOH to neutralize, and adding pH 6.8 phosphate buffer to a concentration of 50 mM. The units in a given sample were determined by comparing the time required to coagulate milk to a standard curve prepared using purified chymosin (Sigma, 23.6 Units/mg protein). One unit was defined as the amount of chymosin required to coagulate 1 ml of milk in 1 min at 30° C. (Sigma).

Immunoprecipitation

Milk coagulating activity in Neurospora culture medium was precipitated by rabbit polyclonal anti-prochymosin serum (gift of M. McCaman, Codon). To 1 ml aliquots was added 5.2 µl of anti-prochymosin serum containing 3.8 mg/ml IgG (estimated by SDS-PAGE) or 19.6 µl of normal rabbit IgG (Pierce, 1.02 mg/ml (final IgG concentrations~20 µg/ml)) as a negative control. No serum was added to a third aliquot, but all other manipulations were done (mock). Following overnight incubation at 4° C., 100 µl of 10% *Staphylococcus aureus* cell suspension (Sigma, binding capacity of 130 µg IgG) in phosphate buffered saline, pH 7, were added and incubated 1 hr at 4° C. *S. aureus* cells were pelleted by centrifugation at 2000 rpm for 10 min, and the supernatant was transferred to a fresh tube.

Western Blots

SDS polyacrylamide gel electrophoresis was performed according to Laemmli (1970) 227:680–685. Proteins were electrotransferred to nitrocellulose and detected immunologically according to Towbin et al., (1979) *Proc. Natl. Acad. Sci. USA* 76:4350–4354. Primary antibodies were detected using goat anti-rabbit IgG conjugated to alkaline phosphatase (AP), followed by incubation with the AP substrates (per 15 ml AP substrate buffer: 5 mg Nitro Blue Tetrazolum and 2.5 mg 5-bromo-4-chloro-3-indoyl-phosphate). Nonspecific binding sites on the nitrocellulose were blocked with 5% (w/v) Carnation skim milk.

Results

Tubulin Expression Vector Construction

A genomic DNA fragment comprising the β-tubulin promoter and encoding part of the 5' untranslated mRNA leader was combined with a second genomic DNA fragment comprising a small portion of the β-tubulin carboxyl-terminal open reading frame, the translational stop codon, transcriptional termination signal, and the mRNA polyadenylation signal in a derivative of the *E. coli* plasmid vector pTZ18R (L. A. Rokeach et. al., *Proc. Natl. Acad. Sci. USA* (1988), 85:4832) to generate the *N. crassa* expression vector pTPT1. Both of the above named β-tubulin genomic DNA fragments were obtained from a benomyl resistant β-tubulin allele cloned previously in plasmid pSV50 (Vollmer and Yanofsky, *Proc. Natl. Acad. Sci. USA* (1986) 83:4869–4873).

All sequences necessary for expression of β-tubulin are found on the genomic SalI-HindIII DNA fragment of pSU50 (Vollmer and Yanofsky, *Proc. Natl. Acad. Sci. USA* (1986) 83:4869–4873). To clone the promoter and sequences encoding the 5' untranslated RNA leader, we first subcloned a SalI - EcoRI fragment from pSV50 into pTZ18R (pTt20). A smaller SalI - SfaNI fragment (352 base pairs [bp]) from pTt20 comprising the promoter and encoding the 5' untranslated RNA leader were subcloned into the SalI and XmaI sites of pUC19 (Yanisch-Perron, C., Vieira, J. and Messing, J. *Gene* (1985) 33:103–119). SfaN1 cleaves 10 nucleotides 5' of the translation initiating ATG and leaves a four nucleotide (5'PO$_4$-GGTT) overhang at this site. SfaNI is among the class of restriction endonucleases which cut in sequences flanking an asymmetric DNA recognition sequence; consequently, the sticky ends generated by SfaNI vary according to the sequence of the flanking DNA. The ends generated by SfaNI digestion were treated with the Klenow fragment of DNA polymerase I in the presence of dATP only, leaving a dinucleotide 5'PO$_4$-GG sticky end at the 3' end of the tubulin promoter fragment.

The pUC19 vector was prepared by digestion with XmaI, treating with Klenow and dCTP only, heat inactivation of the Klenow, and SalI digestion. The Klenow treatment of the XmaI sticky end in the presence of only dCTP converts 5'PO$_4$-CCGG to 5'PO$_4$-CC, which is complementary to the modified SfaNI end of the tubulin promoter. Ligation of the tubulin promoter fragment into pUC19 prepared in this manner yields pUC5'T, which was confirmed by dideoxynucleotide sequencing.

The genomic DNA fragment comprising the *N. crassa* β-tubulin translational and transcriptional stops and the transcript polyadenylation signal was initially subcloned from pSV50 as a BamHI - HindIII fragment into pTZ18R (pt3'BH). This 620 bp fragment contains codons for the carboxyl terminal 103 amino acids of β-tubulin.

The codons for 79 of these amino acids were removed by Exonuclease III (ExoIII) treatment of pt3'BH, leaving sequence encoding only the carboxyl terminal 24 amino acids. Plasmid pt3'BH was digested with restriction endonucleases KpnI and BamHI, incubated with ExoIII, treated with single stranded nuclease S1 to make the ends blunt, and recircularized with T4 DNA ligase. The resulting plasmid, pt3'CassI contains a 381 bp insert from the 3' end of the β-tublin genomic clone as determined by DNA dideoxynucleotide sequencing.

To provide additional restriction endonuclease sites at the 5' end of this tubulin 3' fragment, the SacI - HindIII fragment from pt3'CassI was transferred to the XbaI and HindIII sites of pTZ18R. pt3'CassI was digested with SacI, treated with T4 DNA polymerase whose 3'→5' exonuclease activity removes the four nucleotide 3'-OH tail, and digested with HindIII. Vector pTZ18R was digested with Xba I, treated with Klenow to produce a blunt end, and digested with HindIII. The β-tubulin 3' fragment ligated into this prepared vector yielded pt3'CassI.

The tubulin promoter fragment from pUC5'T and the fragment with the tubulin transcriptional stop and polyadenylation signals (terminator fragment) were combined to produce the tubulin expression vector pTPT1. pTPT1 was made in a derivative of pTZ18R, pTZ18Rat2 from which all but the HindIII, SphI, and PstI restriction endonuclease sites had been removed from the multiple cloning site by exonuclease digestion. pTZ18RAT2 was digested with HindIII and treated with calf intestinal phosphatase to prevent recircularization. The HindIII - KpnI tubulin promoter and the KpnI - HindIII tubulin terminator fragments were isolated from pUC5'T and pt3'CassII, respectively, by agarose gel purification, and the two tubulin fragments were ligated into the HindIII site of pTZ18RAT2. The resulting plasmid pTPT1 has three unique restriction endonuclease sites (KpnI, SmaI, and BamHI) between the tubulin promoter and terminator.

Chymosin cDNA

The bovine chymosin cDNA-containing plasmid, pBC8 (the DNA and sequence information were a gift of Dr. M. McCaman, Codon), contains a BclI fragment from a cDNA clone inserted at the BamHI site of pUC8. Plasmid pBC8 has three ATGs 5' of the start of translation, and computer analysis of the pBC8 sequence demonstrated that the first 148 bp of the cDNA insert are in fact an inverted duplication of part of the ninth (the last) exon of chymosin. The last seven nucleotides of this inverted repeat are homologous to the 6th through 12th nucleotides of the cDNA sequence (Harris, T. J. R., Lowe, P. A., Lyons, A., Thomas, P. G., Eaton, M. A. W. Millican, T. H., Patel, T. P., Bose, C. C., Carey, N. H., and Doel, M. T. *Nucl. Acid Res.* (1982) 10:2177–2187) of the chymosin mRNA; thus the first 141 nucleotides of the cDNA insert are extraneous, and the first five nucleotides of the mRNA are absent from pBC8.

To remove the duplicated exon 9 sequences, the 5' end of the cDNA insert was digested with ExoIII and S1 nucleases. The exonuclease reaction was stopped at various time points, and the DNA was further digested with HindIII, which cuts at the 3' end of the cDNA. DNAs from various time points of the ExoIII digestion were gel purified and subcloned into the HincII and HindIII sites of pTZ18R. Insert sizes of several of these plasmid DNAs were estimated by agarose gel electrophoresis of restriction enzyme digested DNAs, and the exact endpoint of three candidate clones were determined by dideoxynucleotide sequencing. One of these clones, pBC18HH, lacked all but three of the 141 duplicated nuleotides.

Subclonign Chymosin cDNA into Neurospora Expression Vectors

The bovine chymosin cDNA clone pBC18HH was expressed in *N. crassa* using two different expression vectors: pTPT1 described above and pMTF52 described below. Construction of the β-tubulin/chymosin fusion in pTCT is described. To insert the chymosin cDNA fragment into pTPT1, the fragment was removed from pBC18HH by digesting partially with KpnI and completely with HincII. There is one KpnI site within the chymosin open reading frame. Partial KpnI digestion and agarose gel purification selected those DNA molecules that were uncut at that internal site.

The vector pTPT1 was prepared to receive the above chymosin fragment by digesting the unique KpnI and BamHI sites between the promoter and terminator. The chymosin cDNA fragment was mixed with the vector and the complementary KpnI sites were ligated. The BamHI sticky end of the vector was then made blunt by treating with Klenow in the presence of all four deoxynucleotide triphosphates, following which the ligation was continued to ligate the blunt HincII end to the blunted BamHI end.

The second *N. crassa* expression vector used for these studies is based on the grg-1 gene (McNally and Free, (1988) Curr. Genet. 14(6):545–552).

GRG-1 is a glucose-repressible gene which encodes an abundant mRNA in glucose deprived cells (McNally, M. J. and Free, S. S. 1988, (*Current Genetics* (1988) 14(6):545–551); a function for the proposed 7,000 dalton protein is as yet unknown. Originally cloned as a cDNA, a genomic fragment comprising the transcriptional promoter, the transcribe sequences including an open reading frame punctuated by two introns, and 3 flanking sequences including a potential polyadenylation signal has been cloned and developed into several expression vectors (Free, personal communication). pMTF52, used in this study, contains 67 nucleotides of the untranslated leader sequence preceding a unique XhoI site, followed by the GRG-1 open reading frame, the *E. coli* β-glucuronidase encoding sequence, and the GRG-1 polyadenylation site. To facilitate subcloning in the grg-1-based expression vector pMTF52, an XhoI linker was inserted at the XbaI site 5' of the chymosin cDNA sequence in pBC18HH to yield pBC18XH.

Addition of the XhoI linker (sequence 5'CCTCGAGG3') used the technique of Seth (Seth, A., 1984, *Gene Anal. Tech.*, 1: 99–103). pBC18HH was digested with XbaI, treated with Klenow to make the ends blunt, a nonphosphorylated XhoI linker single was ligated to the ends of pBC18HH, and the excess, unligated linkers were removed by spin-column chromatography through Sephadex™ G50. The unligated linker strands were then removed by heating to 90° C. for one minute, quick cooled, and the 5'OH of the DNAs were phosphorylated using polynucleotide kinase and ATP.

The eight nucleotide single-stranded tails of the plasmid were then annealed and ligated with T4 DNA ligase. The SalI-XhoI fragment from pBC18XH was then subcloned into the XhoI site of pMTF52 to yield pGRC52.

Expression of chymosin from this plasmid uses the translation initiating ATG and the secretion signal peptide of chymosin. Sequence of the mRNA encompassing the untranslated leader and the first 37 amino acids of preprochymosin is as follows:

Transcript Sequence of pGRC52

A portion of the grg-1/chymosin fusion transcript comprising the 5' untranslated grg-1 leader and the first 110 nucleotides of the chymosin open reading frame are presented below. The putative transcriptional start at position –106 was proposed by McNally and Free (1988) supra. grg-1 sequences are in lower case, the XhoI linker sequence is in lower case and underlined, and the bovine chymosin sequences are uppercase. The amino terminal S7 amino acids of preprochymosin shown with the beginning of prochymosin indicated.

```
       -100        -90        -80        -70        -60
    caucauc  agccaacaaa  gcaaucacau  cuucacuacu  ucaaaucaac -50        -40        -30
    acaacacuca  aaccacuuuc  ccucgaggCU
                                   pre→

-20        -10          1         10         20
    AGAGUCUCCC  GGCUGGACCC  AGAUCCAAG  AUGAGGUGUC  UCGUGGUGCU
                                       MetArgCys   LeuValValLeu
                                  pro→

30         40         50         60         70
    ACUUGCUGUC  UUCGCUCUCU  CCCAGGGCGC  UGAGAUCACC  AGGAUCCCUC
    LeuAlaVal   PheAlaLeu   SerGlnGlyAla  GluIleThr   ArgIlePro 80         90         110        110
    UGUACAAAGG  CAAGUCUCUG  AGGAAGGCGC  UGAAGGAGCA
    LeuTyrLysGly  LysSerLeu   ArgLysAla   LeuLysGluHis
```

Expression of Bovine Chymosin by *N. crassa*

Bovine chymosin is synthesized in the calf's fourth stomach as a preproenzyme of molecular weight (MW) 42,000 daltons. It is processed to the proenzyme (40,400 MW) during secretion, and in acidic conditions (below pH 5) it is converted to the active enzyme (35,6000 MW) autocatalytically. *N. crassa* strain his-2; mtr was used for these bovine chymosin expression studies. Transformation of *N. crassa* strain his-2; mtr was accomplished by cotransformation with cosmid 6:11E his-2 and selecting for prototrophs. Transformed colonies were picked to slants, and only those which showed a normal growth rate, indicating stable 6:11E transformation, were analyzed further. Conidia from 21 stable transformants were used to inoculate 5 ml Vogel's tryptone broth cultures, and culture medium on day 2 was qualitatively assayed for milk coagulating activity. Whereas cultures of cells containing 6:11E only (strain 6:11E) failed to coagulate milk, 14 cultures of cells containing both pGRG52 and 6:11E did coagulate milk. Seven of these clotted milk within 1 hour and seven others clotted milk within six hours. One pGRC52 transformant, strain 63, had significantly greater coagulating ability than the other transformants, being able to clot milk within 6 minutes. The remaining studies concentrated on strain 63.

The milk coagulating ability of strain 63 was shown to be immune precipitable. Culture medium from 5 day cultures of strains 63 and 6:11E were tested for coagulating activity, which was found only in strain 63's culture medium. No activity was found associated with strain 6:11E. Three 1 ml aliquots of strain 63 culture medium were incubated overnight in the presence of either 1) rabbit anti-prochymosin serum, 2) rabbit nonimmune serum, or 3) no serum, and antibody-protein complexes were precipitated the following day with fixed *S. aureus* cells. The supernatants from samples 2) and 3) as well as untreated culture medium retained clotting ability, whereas sample 1) incubated with anti-prochymosin antibody lost all milk coagulating ability. We conclude that milk coagulating ability expressed by strain 63 is due to chymosin and not a Neurospora protease, and that the soluble chymosin is secreted from the cell.

To determine the efficiency with which chymosin is secreted using its own secretion signal peptide, we examined antigenic material detected on Western blots of intra- and extracellular proteins of strain 63. The results indicate that the majority of chymosin is secreted from the cell. Western blots of these gels probed with the rabbit anti-prochymosin serum specifically identified a band with the expected molecular weight of chymosin (35,600 daltons). This band was found in untreated, and in pH 4.5 and pH 2 treated medium, suggesting that prochymosin is converted to chymosin following secretion. This could be attributed to the drop in pH observed during growth of Neurospora cultures, and agrees with our observation of milk coagulating activity observed in untreated culture medium. In the pH 2 treated sample, a second slightly larger band is seen, which may be attributed to pseudochymosin generated at this low pH.

To estimate the specific activity for the chymosin found in Neurospora culture medium, we quantitated the amount of chymosin by Western blot analysis. In the growth medium of a 5 day culture, we found 0.03 Units/ml of coagulation activity and estimated the amount of chymosin at 500 ng/m (~50 ng per 2.5 µl of 40× concentrated sample) for a specific activity of 60 units/mg protein. This compares favorably to the highest specific activity chymosin available from Sigma (Product #R4879,60 units per mg protein).

Milk clotting activity obtained with pTCT transformants of strain his-2, mtr were comparable to that obtained from strain 63. Conidial isolates displayed various levels of secreted chymosin. Strain 11 was subcultured to apparent homozygosity following transformation. We estimated that subculture strain 11/3 can produce milligram amounts of biologically active chymosin per liter when grown in static cultures.

It is evident from the above results that Neurospora provides an effective and efficient system for the expression and processing of heterologous genes. Thus, commercial systems may be developed which provide for highly efficient production of heterologous genes in biologically active form. These products may be readily isolated and purified to provide economic production of protein products.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of producing a mammalian peptide in a Neurospora fungus host, said method comprising:

transforming by DNA uptake Neurospora spheroplasts with (1) a DNA construct comprising as operably linked components a constitutive promoter functional in said fungus host, a first DNA sequence encoding a mammalian peptide under the transcriptional regulation of said promoter and a transcriptional termination regulatory region functional in said host, and (2) a second DNA sequence comprising a marker gene which is expressed in said host;

selecting for transformed host cells comprising said construct by means of said marker gene;

identifying stably transformed host cells; and growing said stably transformed host cells whereby said first DNA sequence is expressed, and said cells produce said mammalian peptide.

2. A method of producing a mammalian peptide in a *Neurospora crassa* host, said method comprising:

transforming by DNA uptake *N. crassa* spheroplasts with (1) a DNA construct comprising as operably linked components a β-tubulin promoter functional in said host, a first DNA sequence encoding a mammalian peptide under the transcriptional regulation of said β-tubulin promoter and a transcriptional termination regulatory region functional in said host, and (2) a second DNA sequence comprising a marker gene which is expressed in said host;

selecting for transformed host cells comprising said construct by means of said marker gene;

identifying stably transformed host cells; and growing said stably transformed host cells whereby said first DNA sequence is expressed, and said cells produce said mammalian peptide.

3. A DNA construct comprising a Neurospora β-tubulin promoter and a DNA sequence encoding a mammalian peptide under the transcriptional control of said promoter.

4. A DNA construct according to claim 3, wherein said mammalian peptide is preprochymosin.

5. A stably transformed Neurospora cell containing a DNA construct comprising as operably linked components β-tubulin promoter functional in said cell, a first DNA sequence encoding a mammalian peptide under the transcriptional control of said β-tubulin promoter and a transcriptional termination regulatory region functional in said cell; and a second DNA sequence comprising a marker gene expressed in said cell.

6. A Neurospora cell according to claim 5, wherein said mammalian peptide is preprochymosin.

7. A Neurospora cell according to claim 5, which produces a mature mammalian peptide as a result of transcription of said first DNA sequence and translation of the resulting RNA.

8. A Neurospora cell according to claim 7, wherein said mature mammalian peptide is chymosin.

9. A method of producing and secreting in a *Neurospora crassa* host a mammalian peptide said method comprising:

transforming by DNA uptake *N. crassa* spheroplasts with (1) a DNA construct comprising as operably linked components a β-tubulin promoter, an open reading frame comprising a signal sequence for secretion joined to and in reading frame with a first DNA sequence encoding a mammalian peptide under the transcriptional regulation of said promoter and a transcriptional termination regulatory region functional in said host, and (2) a second DNA sequence comprising a marker gene which is expressed in said host;

selecting for transformed host cells comprising said construct by means of said marker gene;

identifying stably transformed host cells; and growing said stably transformed host cells whereby said first DNA sequence is expressed, and said cells produce and secrete said peptide.

10. A stably transformed Neurospora cell containing a DNA construct comprising as operable components a Neurospora β-tubulin promoter and a first DNA sequence encoding a mammalian peptide under the transcriptional control of said promoter and a transcriptional termination regulatory region functional in said cell; and a second DNA sequence comprising a marker gene which is expressed in said cell.

11. A stably transformed *Neurospora crassa* cell containing a DNA construct comprising as operable components a β-tubulin promoter and a first DNA sequence encoding a mammalian peptide under the transcriptional control of said promoter and a transcriptional termination regulatory region functional in said cell; and a second DNA sequence comprising a marker gene which is expressed in said cell.

12. An isolated DNA construct comprising a Neurospora β-tubulin promoter and wherein said DNA construct is substantially free of a β-tubulin open reading frame which expresses β-tubulin.

13. A method of obtaining a mammalian peptide, said method comprising:

isolating said mammalian peptide from a culture broth of stably transformed Neurospora fungus cells which produce said mammalian peptide, wherein said Neurospora fungus cells are derived from spheroplasts transformed by DNA uptake with a DNA construct comprising as operably linked components, a promoter functional in said Neurospora fungus cells, a first DNA sequence encoding a mammalian peptide under the transcriptional regulation of said promoter and a transcriptional termination regulatory region functional in said Neurospora fungus cells, a second DNA sequence comprising a marker gene which is expressed in said Neurospora fungus cells and a third DNA sequence encoding a secretion signal peptide joined to and in reading frame with said first DNA sequence.

14. A method of obtaining a mammalian peptide, said method comprising:

isolating said mammalian peptide from a culture broth of stably transformed *Neurospora crassa* cells which produce said mammalian peptide, wherein said *Neurospora crassa* cells are derived from spheroplasts transformed by DNA uptake with a DNA construct comprising as operably linked components, a promoter functional in said *Neurospora crassa* cells, a first DNA sequence encoding a mammalian peptide under the transcriptional regulation of said promoter and a transcriptional termination regulatory region functional in said *Neurospora crassa* cells, a second DNA sequence comprising a marker gene which is expressed in said *Neurospora crassa* cells and a third DNA sequence encoding a secretion signal peptide joined to and in reading frame with said first DNA sequence.

15. The method according to claim 13 or claim 14, wherein said first DNA sequence encodes chymosin.

16. The method according to claim 13 or claim 14, wherein said first DNA sequence encodes blood protein Factor VIII.

17. The method according to claim 13 or claim 14, wherein said first DNA sequence encodes tissue plasminogen activator.

18. The method according to claim 13 or claim 14, wherein said first DNA sequence encodes serum albumin.

19. The method according to claim 13 or claim 14, wherein said first DNA sequence encodes a growth factor.

20. The method according to claim 13 or claim 14, wherein said first DNA sequence encodes an interleukin.

21. The method according to claim 13 or claim 14, wherein said first DNA sequence encodes a neurotrophin.

22. The method according to claim 13 or claim 14, wherein said promoter is a constitutive promoter.

23. The method according to claim 14, wherein said constitutive promoter is the β-tubulin promoter.

24. The method according to claim 13 or claim 14, wherein said promoter is derived from a grg-1 promoter.

25. The method according to any one of claims 13 or 14, wherein said spheroplasts are derived from an auxotrophic mutant of a Neurospora fungus, and said a marker gene provides complementation of said auxotrophic mutant to prototropy.

26. The method according to claim 25, wherein said auxotrophic mutant is unable to synthesize an essential amino acid.

27. A method of obtaining a mammalian peptide, said method comprising:

isolating said mammalian peptide from a culture broth of stably transformed Neurospora fungus cells which produce said mammalian peptide, wherein said Neurospora fungus cells are derived from spheroplasts transformed by DNA uptake with a DNA construct comprising as operably linked components, a Neurospora β-tubulin promoter, a first DNA sequence encoding a mammalian peptide under the transcriptional regulation of said promoter and a transcriptional termination regulatory region functional in said Neurospora fungus cells, a second DNA sequence comprising a marker gene which is expressed in said Neurospora fungus cells and a third DNA sequence encoding a secretion signal peptide joined to and in reading frame with said first DNA sequence.

28. The method according to claim 27, wherein said mammalian peptide is preprochymosin.

29. The method according to claim 27, wherein said secretion signal peptide is derived from a secretion signal peptide of chymosin.

30. Stably transformed Neurospora fungus cells which produce a mammalian peptide.

31. Stably transformed Neurospora fungus cells which secrete a mammalian peptide.

* * * * *

UNITED STATES PATENT AND TRADEMARK OFFICE
CERTIFICATE OF CORRECTION

PATENT NO. : 5,695,965
DATED : Dec. 9, 1997
INVENTOR(S) : W. Dorsey Stuart, et al It is certified that error appears in the above-identified patent and that said Letters Patent is hereby corrected as shown below:

Column 8, line 22, "S7" should read --37--.

Column 8, line 23, after "preprochymosin" insert --are--.

Columns 7-8, Sequence between lines 24-42, move --("pre →" above the line instead of below; same for "pro→").

Column 9, line 36, "500 ng/m" should read --500 ng/ml--.

Signed and Sealed this

Sixteenth Day of June, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,695,965
DATED : December 9, 1997
INVENTOR(S) : Stuart, et al

It is certified that error appears in the above-identified patent and that said Letters Patent is hereby corrected as shown below:

Columns 7-8, Sequence between lines 24-42 "cucgag" should read --<u>cucgag</u>--.

Signed and Sealed this

Tenth Day of November 1998

Attest:

BRUCE LEHMAN

Attesting Officer

Commissioner of Patents and Trademarks